United States Patent
Grudem, Jr. et al.

(10) Patent No.: US 12,053,166 B2
(45) Date of Patent: *Aug. 6, 2024

(54) CYTOLOGY SAMPLING SYSTEM AND METHOD OF UTILIZING THE SAME

(71) Applicant: Covidien LP, Mansfield, MA (US)

(72) Inventors: Jerome K. Grudem, Jr., Rogers, MN (US); Jay G. Johnson, Maple Plain, MN (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,329

(22) Filed: Jan. 20, 2023

(65) Prior Publication Data

US 2023/0149001 A1 May 18, 2023

Related U.S. Application Data

(63) Continuation of application No. 16/810,997, filed on Mar. 6, 2020, now Pat. No. 11,559,291, which is a
(Continued)

(51) Int. Cl.
| | |
|---|---|
| *A61B 10/02* | (2006.01) |
| *A61B 5/06* | (2006.01) |
| *A61B 10/04* | (2006.01) |

(52) U.S. Cl.
CPC ............ *A61B 10/02* (2013.01); *A61B 5/065* (2013.01); *A61B 10/04* (2013.01); *A61B 2010/0216* (2013.01); *A61B 2010/045* (2013.01)

(58) Field of Classification Search
CPC .......... A61B 10/02; A61B 5/065; A61B 10/04; A61B 2010/0216; A61B 2010/045
See application file for complete search history.

(56) References Cited

U.S. PATENT DOCUMENTS

| 2,677,840 A | * | 5/1954 | Morton ................... A47L 21/02 |
| | | | D32/42 |
| 2,739,585 A | | 3/1956 | Ernest |

(Continued)

FOREIGN PATENT DOCUMENTS

| JP | H10179593 A | 7/1998 |
| WO | 0010456 A1 | 3/2000 |

(Continued)

OTHER PUBLICATIONS

European Office Action dated Oct. 27, 2015, issued in European Application No. 14 154 619.
(Continued)

*Primary Examiner* — Rene T Towa
(74) *Attorney, Agent, or Firm* — Carter, DeLuca & Farrell LLP

(57) ABSTRACT

A cytology sampling system includes a catheter tube and a cytology tool. The catheter tube has open proximal and distal ends. The cytology tool is insertable through the catheter tube and includes a flexible shaft and a brush. The brush is coupled to the distal end of the flexible shaft. The brush includes a plurality of brush shafts. Each brush shaft has bristles disposed along a portion of a length thereof. The bristles are coupled to and extend radially away from an outer surface of each of the brush shafts. The bristles are configured to collect cell samples from targeted tissue of a patient.

20 Claims, 10 Drawing Sheets

Related U.S. Application Data continuation of application No. 14/176,256, filed on Feb. 10, 2014, now Pat. No. 10,595,830.

(60) Provisional application No. 61/763,316, filed on Feb. 11, 2013.

(56) References Cited

U.S. PATENT DOCUMENTS

| | | | |
|---|---|---|---|
| 2,847,990 A | | 8/1958 | Ernest |
| 4,245,653 A * | | 1/1981 | Weaver ............ A61B 10/0291 600/569 |
| 4,966,162 A * | | 10/1990 | Wang .................... A61B 10/04 600/565 |
| 5,191,899 A | | 3/1993 | Strickland et al. |
| 5,611,361 A * | | 3/1997 | Leone .................... A46B 9/021 132/142 |
| 6,188,355 B1 | | 2/2001 | Gilboa |
| 7,543,348 B2 * | | 6/2009 | Le ....................... A46B 5/0012 15/23 |
| 9,459,770 B2 | | 10/2016 | Baker |
| 10,595,830 B2 | | 3/2020 | Grudem, Jr. et al. |
| 11,559,291 B2 | | 1/2023 | Grudem, Jr. et al. |
| 2002/0165467 A1 | | 11/2002 | Rutenberg |
| 2005/0182295 A1 | | 8/2005 | Soper et al. |
| 2005/0256426 A1 * | | 11/2005 | Brugge .................. A61B 10/04 600/569 |
| 2006/0184016 A1 | | 8/2006 | Glossop |
| 2007/0032723 A1 | | 2/2007 | Glossop |
| 2009/0326414 A1 | | 12/2009 | Peltier |
| 2010/0241028 A1 | | 9/2010 | Johnson et al. |
| 2011/0085720 A1 | | 4/2011 | Averbuch |
| 2012/0046521 A1 | | 2/2012 | Hunter et al. |

FOREIGN PATENT DOCUMENTS

| | | |
|---|---|---|
| WO | 0167035 A1 | 9/2001 |
| WO | 2011161564 A1 | 12/2011 |

OTHER PUBLICATIONS

Australian Examination Report dated Jun. 19, 2017, issued in AU Appln. No. 2014200695.
Australian Office Action dated Mar. 19, 2018 in Australian Appln. No. 2014200695.
Merriam-Webster Dictionary entry for "wire" (http://www.merriam-webster.com/dictionary/wire) (date unknown).
European Search Report dated Apr. 24. 2014 in European Application No. EP 14 15 4619.

* cited by examiner

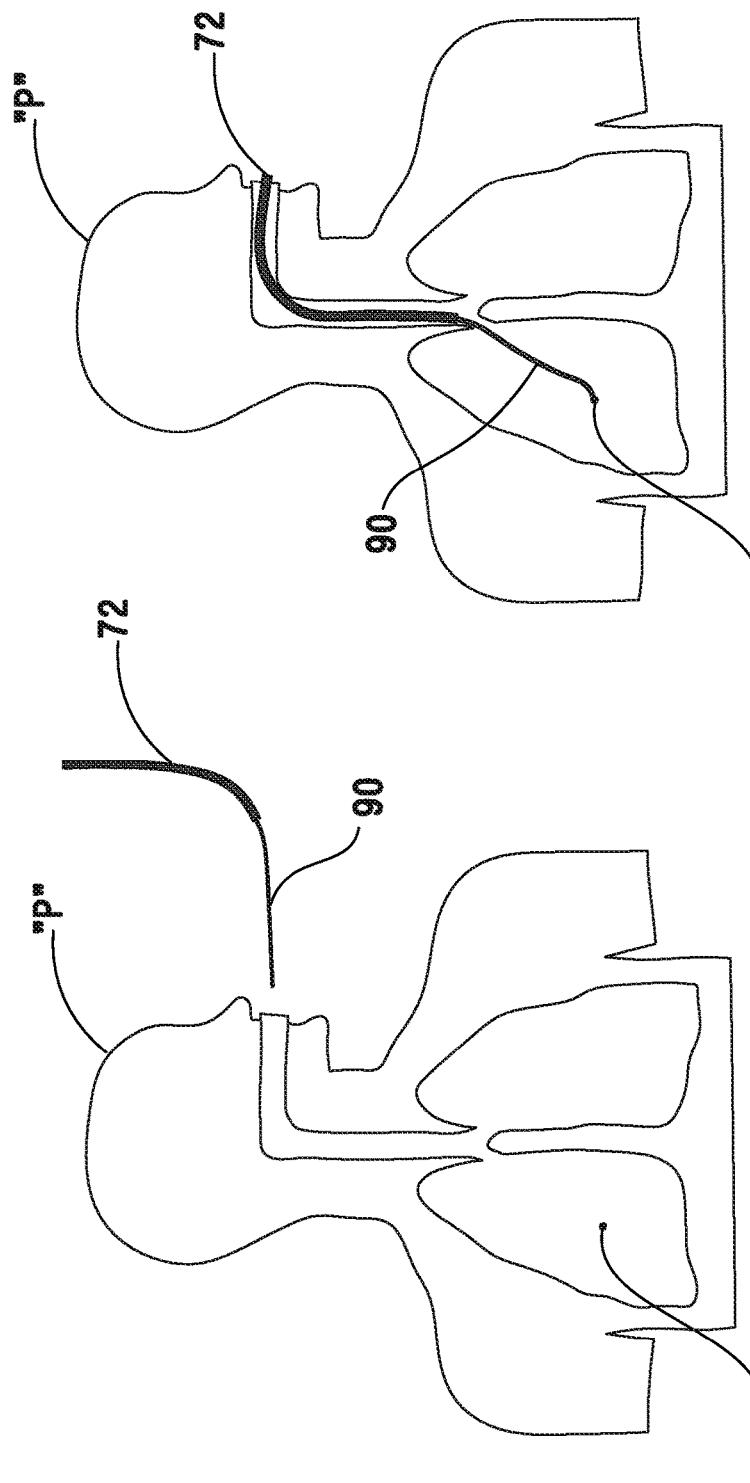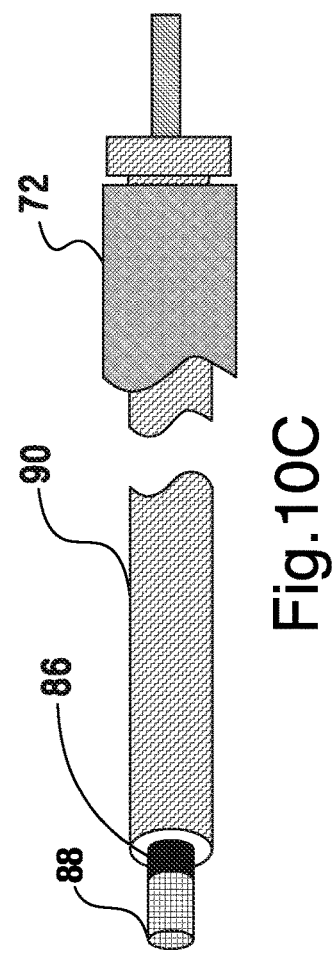

CYTOLOGY SAMPLING SYSTEM AND METHOD OF UTILIZING THE SAME

CROSS REFERENCE TO RELATED APPLICATIONS

This application is a continuation of U.S. patent application Ser. No. 16/810,997, filed on Mar. 6, 2020, now U.S. Pat. No. 11,559,291, which is a continuation of U.S. patent application Ser. No. 14/176,256, filed on Feb. 10, 2014, now U.S. Pat. No. 10,595,830, which claims the benefit of the filing date of provisional U.S. Patent Application No. 61/763,316, filed on Feb. 11, 2013.

INTRODUCTION

The present disclosure relates to the collecting of cell specimens for diagnostic purposes and, more specifically, a cytology sampling tool that is positionable through one or more branched luminal networks of a patient for collecting cell specimens.

BACKGROUND

Cancer can be prevented, treated, and possibly cured if it is detected early enough, preferably in its precancerous or precursor stages. Accordingly, much effort has been directed to developing improvements in early detection devices and of the presence of cancer in its early stages.

Samples that contain more cells provide a greater accuracy and greater likelihood of early detection of the presence of cancer. A continuing need exists for devices capable of collecting larger cell samples form tissue of a patient.

Endobronchial navigation uses CT image data to create a navigation plan to facilitate advancing a navigation catheter (or other suitable device) through a bronchoscope and a branch of the bronchus of a patient to the nodule. Electromagnetic tracking may also be utilized in conjunction with the CT data to facilitate guiding the navigation catheter through the branch of the bronchus to the nodule. In certain instances, the navigation catheter may be positioned within one of the airways of the branched luminal networks adjacent to or within the nodule or point of interest to provide access for one or more tools. Once the navigation catheter is in position, fluoroscopy may be used to visualize cytology tools, such as, for example, biopsy brushes, needle brushes and biopsy forceps as they are passed through the navigation catheter and into the lung and to the nodule or point of interest.

SUMMARY

In an aspect of the present disclosure, a cytology tool includes a flexible shaft, a brush, and a position sensor. The flexible shaft defines proximal and distal ends. The brush is coupled to the distal end of the flexible shaft. The brush includes a plurality of brush shafts each having bristles along a portion of a length thereof. The bristles are coupled to and extend radially away from an outer surface of each of the plurality of brush shafts. The position sensor is configured to provide an indication of the location of the position sensor within a luminal structure. The distal ends of each of the plurality of brush shafts may be biased away from the distal ends of each of the other brush shafts.

In some embodiments, distal ends of each of the plurality of brush shafts include needle tips for penetrating tissue. In certain embodiments, distal ends of each of the plurality of brush shafts are blunt for atraumatically contacting tissue.

In some embodiments, the bristles are helically disposed along a length of each of the brush shafts. The bristles may be disposed along the entire length of each of the brush shafts.

In aspects of the present disclosure, a cytology sampling system includes a catheter tube and a cytology tool. The catheter tube includes open proximal and distal ends. The cytology tool may be any of the cytology tools disclosed herein.

In some embodiments, the brush has a transport configuration such that the distal ends of each the plurality of brush shafts adjacent one another and a deployed configuration such that the distal ends of each of the plurality of brush shafts are spaced-apart from one another. In the transport configuration, the brush may be disposed within the catheter tube between the proximal and distal ends thereof and in the deployed configuration, the brush may extend from the distal end of the catheter tube.

In certain embodiments, the cytology sampling system includes a positioning detection system operatively coupled to the position sensor to determine the location of the position sensor with respect to targeted tissue within a bronchial airway. In particular embodiments, the cytology sampling system may include a locatable guide with a steerable distal tip and a working channel. The steerable distal tip is adapted to position the position sensor adjacent target tissue within a bronchial airway.

In some aspects of the present disclosure, a method of sampling tissue includes identifying the location of a target in a luminal structure, generating a pathway plan to the target, traversing a cytology tool through the luminal network while sensing its location, generating a representation of the cytology tool traversing the luminal network to the target, and contacting the target tissue with bristles of the cytology tool. The cytology tool may be any of the cytology tools disclosed herein. The method may further include inserting the cytology tool through a catheter tube. The method may include extending the bristles of the cytology tool from a distal end of the catheter tube such that the brush shafts bias away from one another. Positioning the distal end of the catheter tube may include inserting the catheter tube through a working channel of a positioning assembly positioned adjacent the target.

In some embodiments, traversing the luminal network includes steering a distal end of the cytology tool to a location adjacent the target with a steerable distal tip. In certain embodiments, the method includes registering a sensed position of the cytology tool to image data of the luminal network. The method may include registering a sensed position of the cytology tool to image data of the luminal network. The method may also include registering the sensed position of the cytology tool to a 3D model of the luminal network.

In certain embodiments, the method includes confirming the placement of the cytology tool using one or more imaging modalities. In particular embodiments, contacting the target tissue includes penetrating the wall of a body lumen with a needle tip of at least one of the plurality of brush shafts to contact the target with bristles of the at least one of the plurality of brush shafts.

Further, to the extent consistent, any of the aspects described herein may be used in conjunction with any or all of the other aspects described herein.

BRIEF DESCRIPTION OF THE DRAWINGS

Various embodiments of the present disclosure are described hereinbelow with references to the drawings, wherein:

FIG. 10A is a schematic, plan view of the extended working channel positioned within a bronchoscope prior to being positioned within a trachea of a patient;

FIG. 10B is a schematic, plan view of the bronchoscope shown in FIG. 10A positioned within the trachea of the patient with the extended working channel extending distally therefrom;

FIG. 10C is a partial, cutaway view of the extended working channel and locatable guide positioned within the bronchoscope;

DETAILED DESCRIPTION

A sampling tool, such as a cytology-sampling tool that is positionable through one or more branched luminal networks of a patient to sample tissue may prove useful in the surgical arena and the present disclosure is directed to such apparatus, systems, and methods. Access to luminal networks may be percutaneous or through a natural orifice. In the case of a natural orifice, an endobronchial approach may be particularly useful in the treatment of lung disease or the like. Targets, navigation, access, and treatment may be planned pre-procedurally using a combination of imaging and/or planning software. In accordance with these aspects of the present disclosure, the planning software may offer custom guidance using pre-procedure images. Navigation of the luminal network may be accomplished using image-guidance. These image-guidance systems may be separate or integrated with the cytology sampling tool or a separate access tool and may include MM, CT, fluoroscopy, ultrasound, electrical impedance tomography, optical, and device tracking systems. Methodologies for locating the separate or integrated to the sampling device or a separate access tool include EM, IR, echolocation, optical, and others. Tracking systems may be integrated into imaging device, where tracking is done in virtual space or fused with preoperative or live images. In some cases, the sampling target may be directly accessed from within the lumen, such as for the sampling of the endobronchial wall for COPD, Asthma, lung cancer, etc. In other cases, the sampling tool and/or an additional access tool may be required to pierce the lumen and extend into other tissues to reach the target, such as for the sampling of disease within the parenchyma. Final localization and confirmation of sampling tool placement may be performed with imaging or navigational guidance using the modalities listed above. The monitoring of the sampling may be monitored from within the lumen or extracorporeally using the image-guidance modalities described above.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
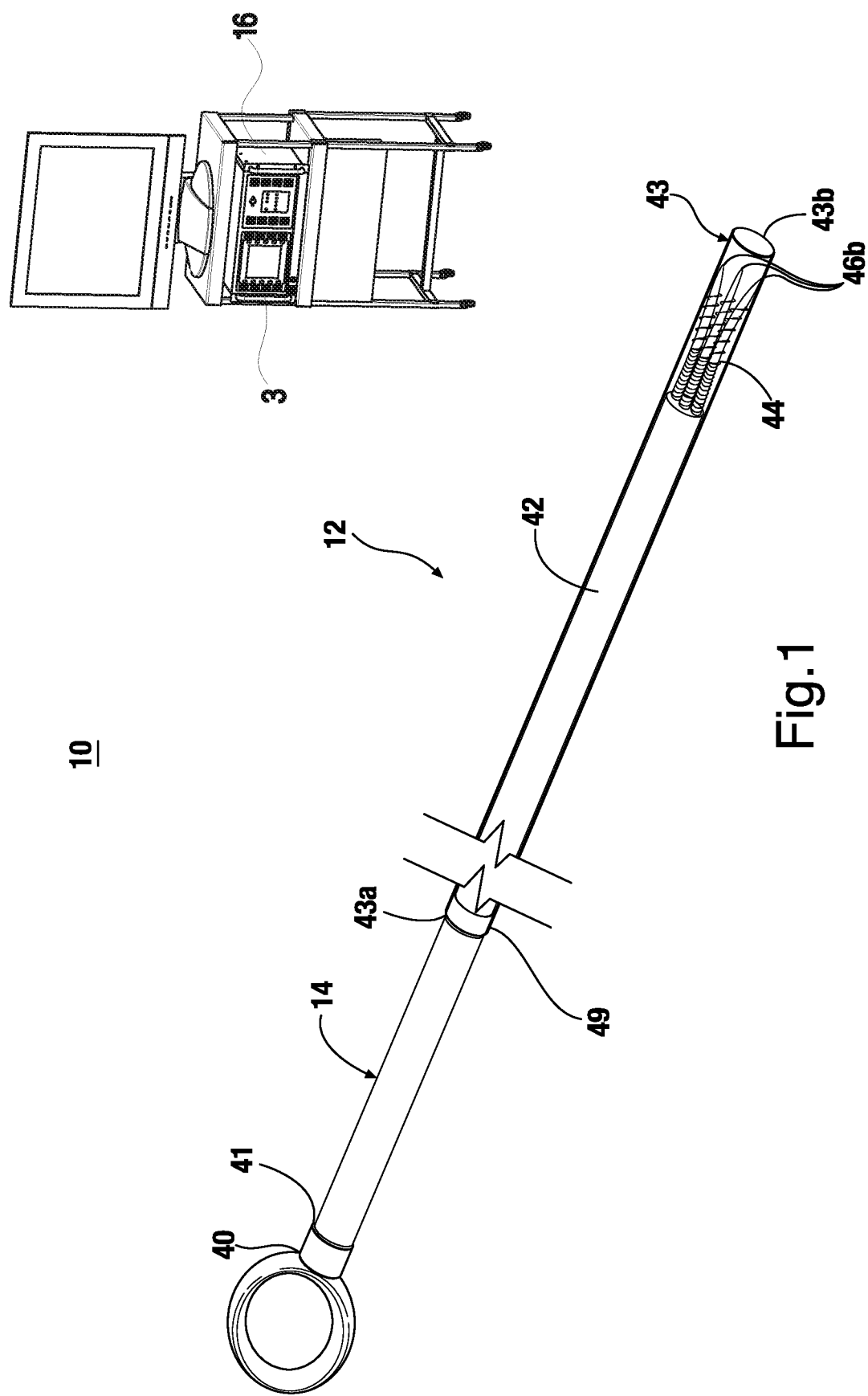
FIG. 1 is a perspective view of a cytology sampling system including a cytology catheter assembly configured for use with the cytology sampling system in accordance with the present disclosure with the brush in a transport configuration.
Figure 2:
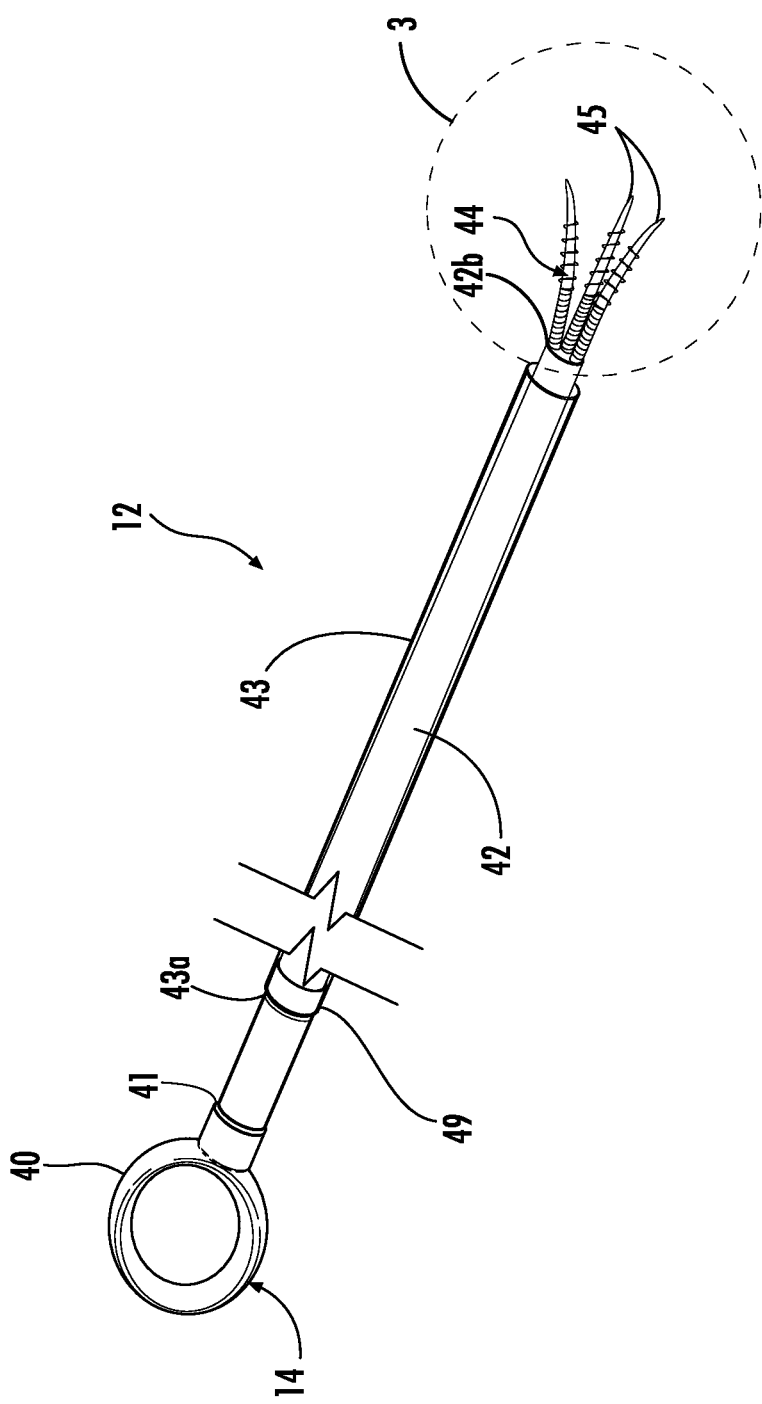
FIG. 2 is a perspective view of the cytology catheter assembly of FIG. 1 with the brush in a deployed configuration.
Figure 3:
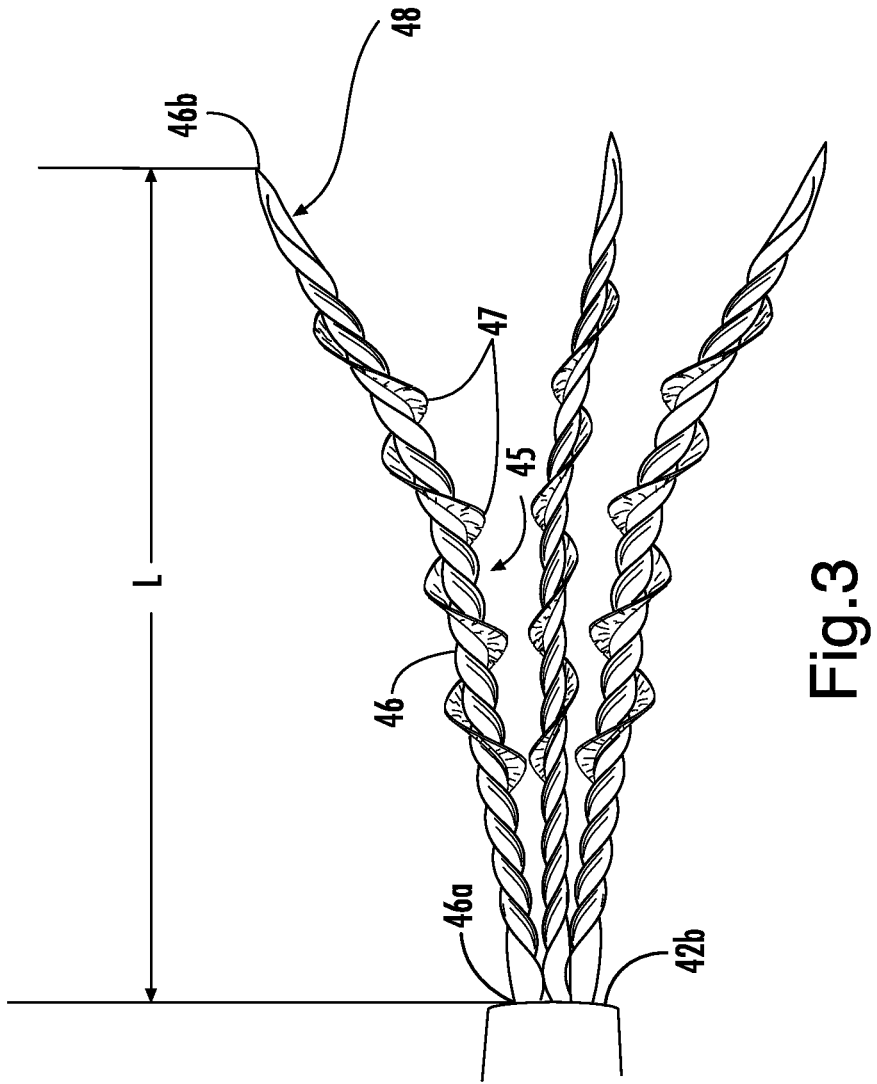
FIG. 3 is an enlarged view of the detail area 3 shown in FIG. 2.

Referring to FIGS. 1-3, a cytology sampling system 10 is provided in accordance with the present disclosure including a cytology catheter assembly 12. The cytology catheter assembly 12 includes a cytology tool 14 and a catheter tube 43 configured to house the cytology tool 14. A proximal end 43a of the catheter tube 43 is open and may include a cuff 49. A distal end 43b of the catheter tube 43 is open. The catheter tube 43 may have an outer diameter in a range of about 1.5 mm to about 2.5 mm, e.g., about 1.92 mm.

The cytology tool 14 includes a handle 40, a flexible shaft 42, and a brush 44. The handle 40 includes a distal handle surface 41 configured to abut the proximal end 43a of the catheter tube 43. A working length of the flexible shaft 42 distally extends from the distal handle surface 41 to the brush 44 and is insertable through the catheter tube 43 as detailed below. The working length of the flexible shaft 42 may be in a range of about 60 cm to about 180 cm, e.g., about 120 cm. The brush 44 is coupled to a distal end 42b of the flexible shaft 42. As shown in FIG. 2, brush 44 includes three brush tips 45; however, it is contemplated that brush 44 may include a fewer or a greater number of brush tips 45. The inclusion of additional brush tips has been shown to increase the number of cells collected from targeted tissue during a sampling procedure.

With particular reference to FIG. 3, each brush tip 45 includes a brush shaft 46, bristles 47, and a tip 48. The brush shaft 46 is flexible and biased away from a longitudinal axis defined by the flexible shaft 42. The bristles 47 cover a portion of the brush shaft 46. In embodiments, the bristles 47 are disposed along an entire length L of the brush shaft 46. In some embodiments, the bristles 47 are helically disposed about a portion of the length L of the brush shaft 46. The bristles 47 are configured to capture tissue, i.e., cells, from targeted tissue. The tip 48 may be a needle tip configured to penetrate tissue. In certain embodiments, the tip 48 may be blunt to atraumatically contact tissue. The brush shaft 46 defines the length L from a proximal end 46a to a distal end 46b thereof. The length L may be in a range of about 10 mm to about 25 mm, e.g., about 15 mm. It is also contemplated that the length L may be less than 10 mm or greater than 25 mm. Each brush shaft 46 may have an outer diameter in a range of about 0.5 mm to about b 1 mm, e.g., about 0.75 mm. The bristles 47 may be constructed of nylon extending in a range of about 0.25 mm to about 1.0 mm, e.g., about 0.85 mm, from the brush shaft 46.

The brush 44 has a transport or insertion configuration (FIG. 1) and a deployed configuration (FIG. 2). In the transport configuration each brush shaft 46 is substantially aligned with the other brush shafts 46 with the distal ends 46b of the brush shafts 46 adjacent one another as shown in FIG. 1. The brush 44 is disposed within the catheter tube 43 such that catheter tube 43 urges each brush shaft 46 into substantial alignment with the longitudinal axis defined by the flexible shaft 42 to substantially align the brush shafts 46 in the transport configuration. In the deployed configuration, the distal ends 46b of the brush shafts 46 are spaced-apart from one another in cooperation with the biasing of the brush shafts 46 as shown in FIG. 2. The brush 44 is disposed outside of the catheter tube 43 permitting the brush shafts 46 to spread-apart into the deployed configuration.

In use, the distal end 43b of the catheter tube 43 is positioned adjacent targeted tissue with the brush 44 in the transport configuration and the distal handle surface 41 of the handle 40 spaced-apart from the proximal end 43a of the catheter tube 43 as shown in FIG. 1. A method for positioning the distal end 43b of the catheter tube 43 adjacent targeted tissue is described in detail below. When the distal end 43b is positioned adjacent the targeted tissue, the distal handle surface 41 of the handle 40 is moved towards the proximal end 43a of the catheter tube 43 to extend the brush 44 from the distal end 43b of the catheter tube 43 as shown in FIG. 2. When the brush 44 extends from the distal end 43b of the catheter tube 43, the brush shafts 46 bias the brush 44 to the deployed configuration. In the deployed configuration, the bristles 47 contact targeted tissue to capturing cell samples from the targeted tissue. When the bristles 47 have captured cell samples, the distal handle surface 41 of the handle 40 is retracted away from the proximal end 43a of the catheter tube 43 to withdraw the brush 44 into the distal end 43b of the catheter tube 43 transitioning the brush 44 into the transport configuration. The cell samples are retained on the bristles 47 of the brush 44 when the brush 44 is withdrawn into the catheter tube 43. The cell samples may be removed from the bristles 47 and examined to determine if the targeted tissue is diseased. It is also contemplated that the catheter tube 43 may be used to aspirate cells adjacent the distal end thereof to retain cell samples.

In embodiments, that the bristles 47 capture tissue between the brush shafts 46 as the brush 44 transitions from the deployed configuration to the transport configuration. For example, the distal ends 46b of the brush shafts 46 may pierce targeted tissue and the catheter tube 43 may be advanced over the brush 44 to transition the brush 44 to the transport configuration such that a portion of the tissue between the brush shafts 46 (i.e., the tissue pierced by the brush shafts 46) is retained between the brush shafts 46 and drawn into the catheter tube 43.

The cytology catheter assembly 12, depicted in FIG. 1 is configured to collect cell samples from targeted tissue, and as further set forth in FIG. 4 enables a method of identifying targeted tissue (hereinafter simply referred to as "a target") utilizing computed tomographic (CT) images, and once identified further enables the use of a navigation or guidance system to position the distal end 43b of the catheter tube 43 adjacent the target. CT data facilitates the planning of a pathway to an identified target as well as providing the ability to navigate through the body to the target location, this includes a preoperative and an operative component (i.e., pathway planning and pathway navigation). As detailed below, the cytology catheter assembly 12 is guided through the lungs of a patient; however, it is contemplated that the cytology catheter assembly 12 may be guided through other tubular structures of a patient; e.g., gastro-intestinal tract, lymphatic system, venous, billiary, etc.

The pathway planning phase is generally described below. First, planning a pathway involves using software for generating and viewing a three-dimensional (3D) model of the bronchial airway tree ("BT") and viewing the CT data to identify targets. Next, the software is used to select a pathway on the BT, either automatically, semi-automatically, or manually, if desired. It is to be understood that the airways are being used herein as an example of a branched luminal network. Hence, the term "BT" is being used in a general sense to represent any such luminal network (e.g., the circulatory system, or the gastro-intestinal tract, etc.)

Figure 4:
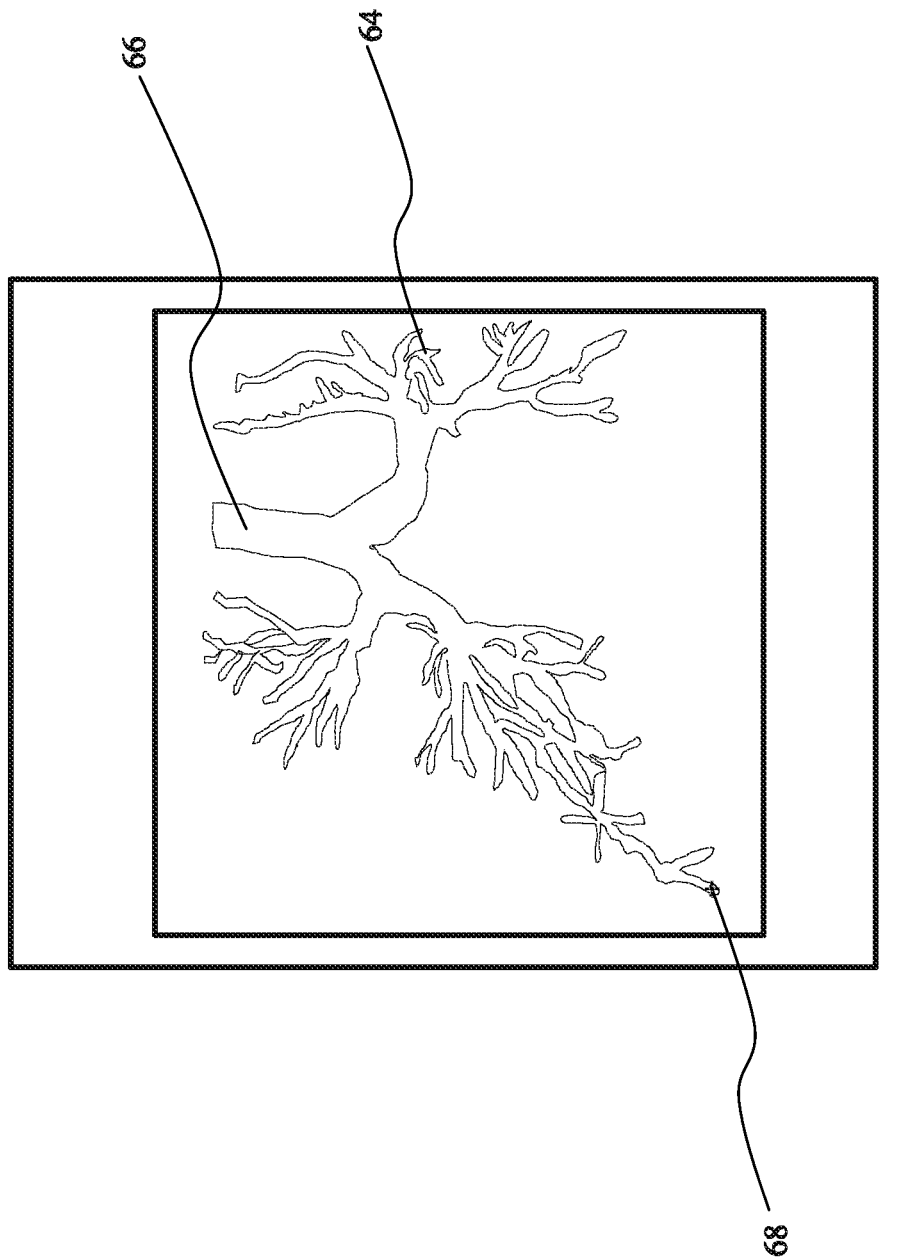
FIG. 4 is a screen shot of a CT based luminal navigation system in accordance with the present disclosure.

Using a software graphical interface 64 as shown in FIG. 4, generating and viewing a BT, starts with importing CT scan images of a patient's lungs into the software. The software processes the CT scans and assembles them into a three-dimensional CT volume by arranging the scans in the order they were taken and spacing them apart according to the setting on the CT when they were taken. The software uses the newly-constructed CT volume to generate a three-dimensional map, or BT, of the airways. The software then displays a representation of the three-dimensional map 66 on the software graphical interface 64. A user may be presented with various views to identify masses or tumors that the medical professional would like to biopsy or treat, and to which the medical professional would like to use the cytology sampling system 10 to navigate.

Next, the software selects a pathway to a target, e.g., target 68 identified by a medical professional. In one embodiment, the software includes an algorithm that does this by beginning at the selected target and following lumina back to the entry point. The software then selects a point in the airways nearest the target. The pathway to the target may be determined using airway diameter. Alternatively, the user rotates the generated volume to identify a convenient entry into the luminal network and the software generates a pathway back to the starting point.

After the pathway has been determined, or concurrently with the pathway determination, the suggested pathway is displayed for user review. This pathway is the path from the trachea to the target that the software has determined the medical professional is to follow for treating the patient. This pathway may be accepted, rejected, or altered by the medical professional. Having identified a pathway in the BT connecting the trachea in a CT image with a target, the pathway is exported for use by cytology sampling system 10 to place a catheter and tools at the target for biopsy of the target and eventually treatment if necessary. Additional methods of determining a pathway from CT images are described in commonly assigned U.S. patent application Ser. No. 13/838,805 entitled "Pathway Planning System and Method" the entirety of which is incorporated herein by reference.

Figure 5:
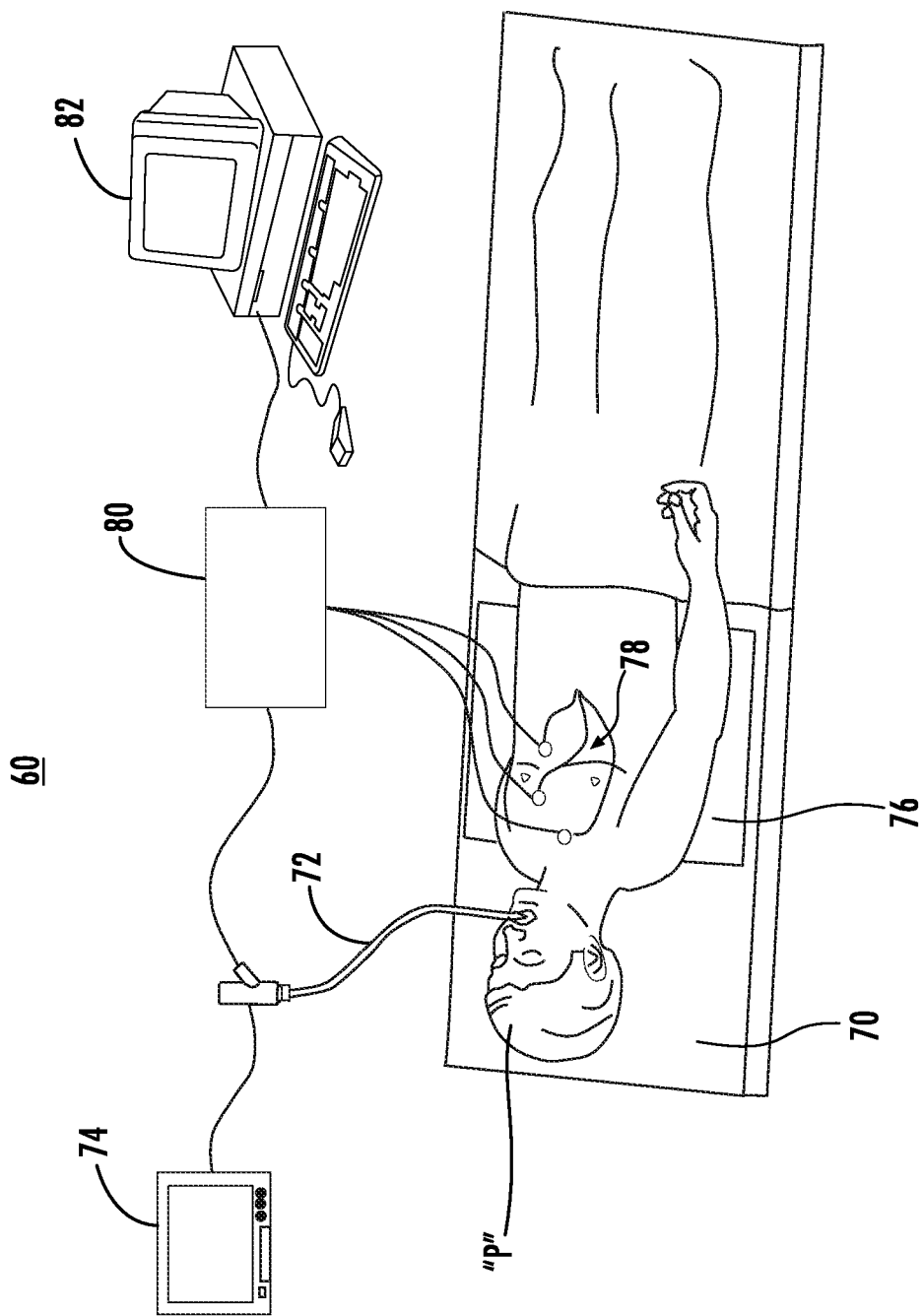
FIG. 5 is a perspective view of a cytology sampling system and luminal navigation system configured for use the cytology catheter assembly shown in FIG. 1 in accordance with the present disclosure.

FIG. 5 shows a patient "P" lying on an operating table 70 and connected to a positioning detection system 60 enabling navigation along the determined pathway within the luminal network to achieve access to the identified target. The positioning detection system 60 includes a bronchoscope 72, monitoring equipment 74, and a tracking module 80. The bronchoscope 72 is inserted into the patient's lungs. The bronchoscope 72 is connected to the monitoring equipment 74 and the tracking module 80, and typically includes a source of illumination and a video imaging system. In certain cases, the devices of the present disclosure may be used without a bronchoscope, as will be detailed below. The tracking module 80 receives sensor data from a variety of sensors enabling the position of the patient "P", the location of the cytology catheter assembly 12, and the image data to be registered to one another thereby permitting navigation of the luminal network using the CT image data and real-time detection of location. Specifically, tracking module 80 utilizes a six DOF (degrees of freedom) electromagnetic position measuring system according to the teachings of U.S. Pat. No. 6,188,355 and published PCT Application Nos. WO 00/10456 and WO 01/67035, which are incorporated herein by reference. An electromagnetic field transmitter 76 is implemented as a board or mat positioned beneath patient "P." A plurality of reference sensors 78 are placed on the patient "P" and their location within the electromagnetic field generated by the electromagnetic field transmitter 76 can be detected. The location of each sensor 78 is determined in six DOF and their six coordinates sent to tracking module 80 and computer 82. One of skill in the art will recognize that the tracking module 80 may be incorporated into computer 82 as a software component and need not be a separate component as depicted in FIG. 5.

Figure 6:
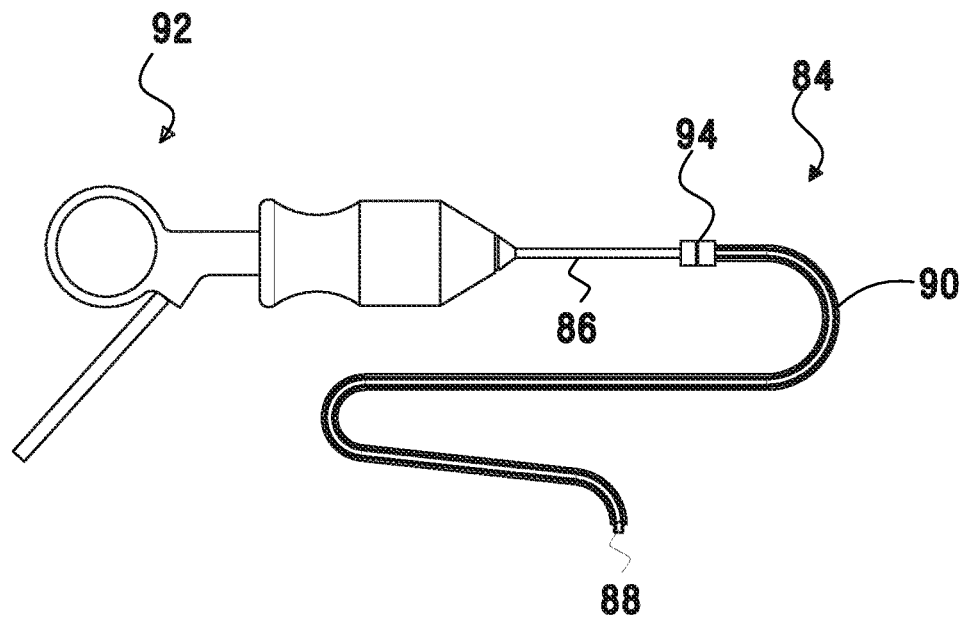
FIG. 6 is a side view of a luminal catheter delivery assembly including an extended working channel and locatable guide catheter in accordance with the present disclosure.
Figure 7:
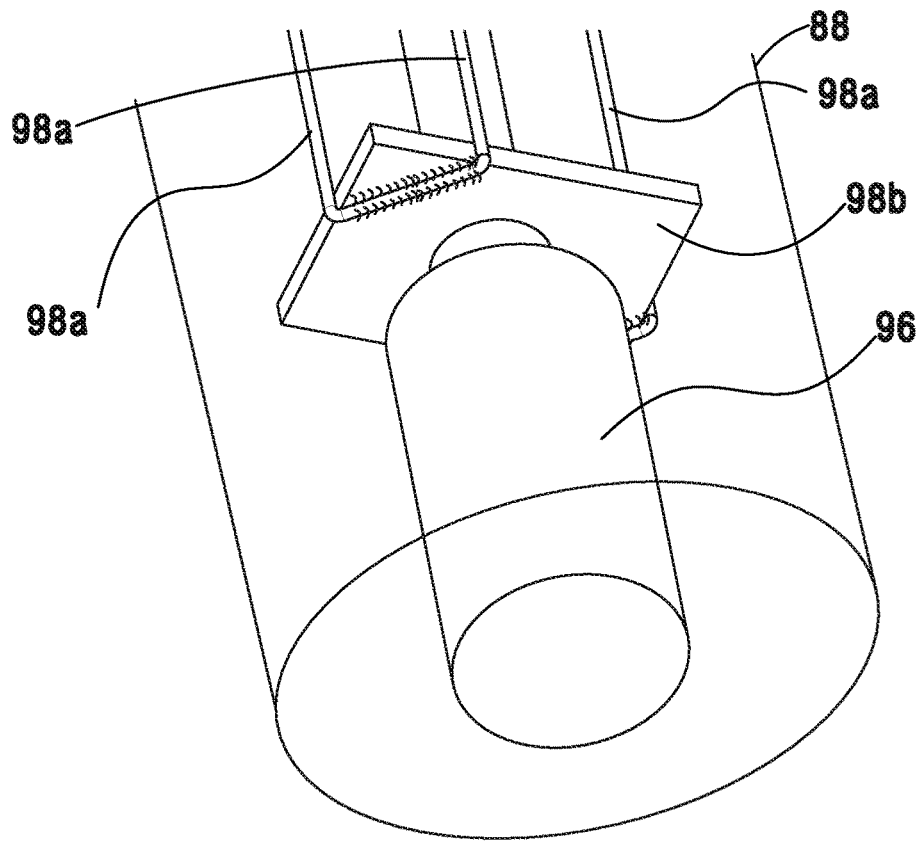
FIG. 7 is a partial, perspective view of a distal end of the locatable guide catheter shown in FIG. 6.

FIG. 6 depicts a positioning assembly 84, constructed and operative according to the teachings of the present disclosure. The positioning assembly 84 includes a locatable guide 86 which has a steerable distal tip 88, an extended working channel 90, and, at its proximal end, a control handle 92.

There are several methods of steering the locatable guide 86, and therewith the extended working channel 90. In a first method, a single direction of deflection may be employed. Alternatively, a multi-directional steering mechanism with a manual direction selector may be employed to allow selection of a steering direction by the practitioner without necessitating rotation of the catheter body. With multi-directional steering four elongated tensioning elements ("steering wires") 98a are implemented as pairs of wires formed from a single long wire extending from handle 92 to steerable distal tip 88. Steering wires 98a are bent over part of a base 98b and return to handle 92. Steering wires 98a are deployed such that tension on each wire individually will steer the steerable distal tip 88 towards a predefined lateral direction. In the case of four steering wires 98a, the directions are chosen to be opposite directions along two perpendicular axes. In other words, the four steering wires 98a are deployed such that each wire, when actuated alone, causes deflection of the steerable distal tip 88 in a different one of four predefined directions separated substantially by multiples of 90°.

Locatable guide 86 is inserted into the extended working channel 90 within which it is locked in position by a locking mechanism 94. A position sensor element 96 is integrated with the steerable distal tip 88 of the locatable guide 86 and allows monitoring of the tip position and orientation (six DOF) as the sensor element 96 traverses the electromagnetic field generated by the electromagnetic field transmitter 76.

Figure 8:
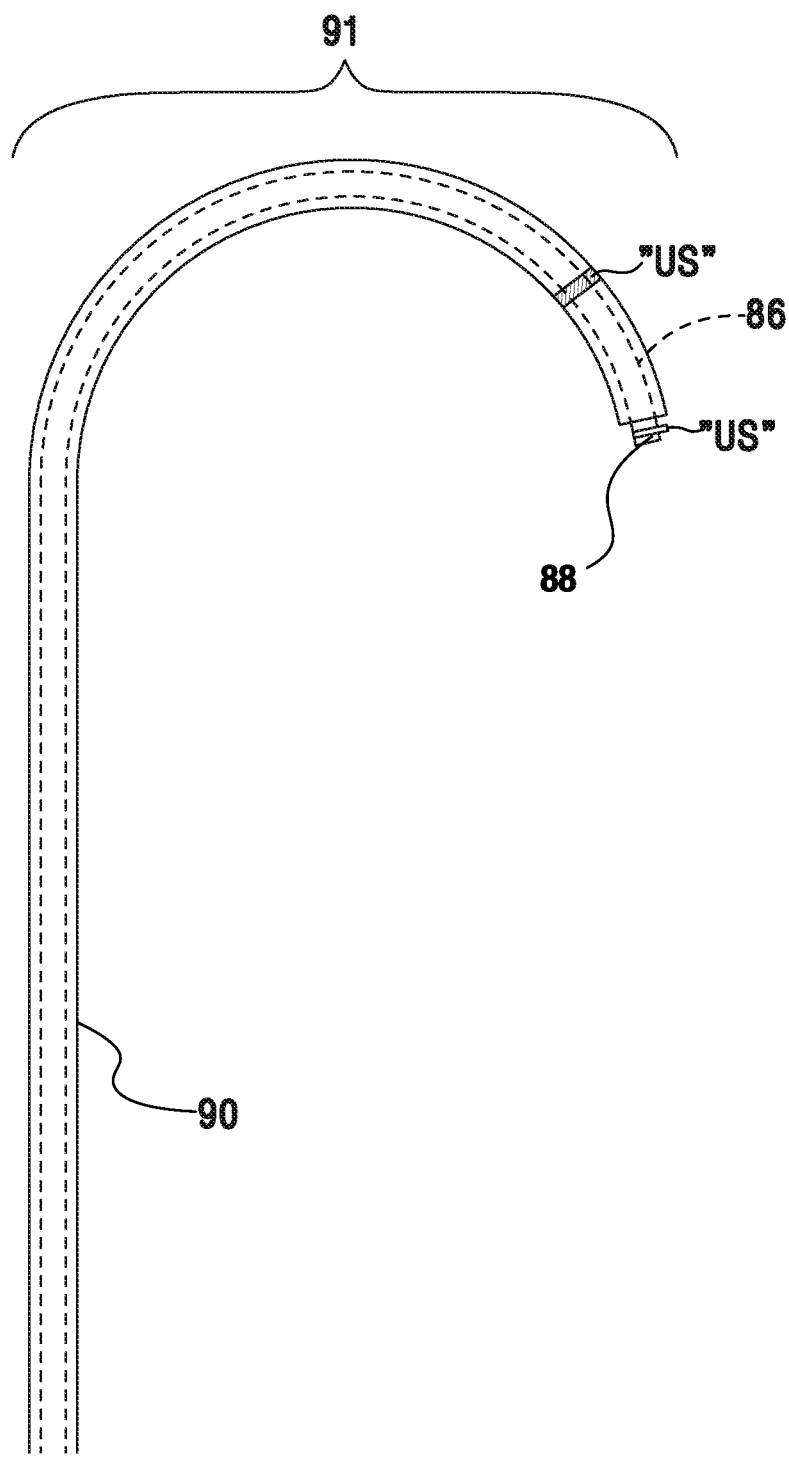
FIG. 8 is a side view of the extended working channel shown in FIG. 7 with the guided tip extending from a distal end thereof.

In embodiments, extended working channel 90 may have a curved or hooked tip configuration 91 as shown in FIG. 8. This alternative is currently marketed by Covidien LP under the name EDGE®. Differing amounts of pre-curve implemented in the extended working channel 90 can be used, however, common curvatures include 45, 90, and 180 degrees. The 180 degree extending working channel 90 has been found particular useful for directing the locatable guide 86 to posterior portions of the upper lobe of the lung which can be particularly difficult to navigate. The locatable guide 86 is inserted into the extended working channel 90 such that the position sensor 96 projects from the extended working channel 90. The extended working channel 90 and the locatable guide 86 are locked together such that they are advanced together into the lung passages of the patient "P." Optionally, the locatable guide 86 or the extended working channel 90 may include a steering mechanism similar to the one described above. As can be appreciated, certain modifications may need to be made to the extended working channel 90 in order for the extended working channel to function as intended.

In embodiments, an integrated radial ultrasound probe "US" (FIG. 8) may be provided on the extended working channel 90, the locatable guide 86, and/or the cytology catheter assembly 12. For illustrative purposes, the ultrasound probe "US" is shown disposed on the extended working channel 90 and the locatable guide 86. The ultrasound probe "US" may be configured to provide ultrasound feedback to one or more modules of the cytology sampling system 10 during navigation and insertion of the cytology tool 14 to facilitate positioning the distal end 43b of the catheter tube 43 adjacent target tissue. As will be appreciated a US probe may also be used without the extended working channel but in conjunction with an endoscope for imaging central lesions that would be accessible to the endoscope. Furthermore, the US probe may be used to conduct ultrasound interrogation of tissue. Alternatively, fluoroscopy or other imaging modalities may be used to confirm the placement of the locatable guide and therewith the extended working channel 90 and the brush 44.

As noted above, the present disclosure employs CT data (images) for the route planning phase. CT data is also used for the navigation phase. Specifically, the CT system of coordinates is matched with the collected sensor data; this is commonly known as registration. Manual, semi-automatic, or automatic registration can be utilized with the cytology sampling system 10. For purposes herein, the cytology sampling system 10 is described in terms of use with automatic registration. Reference is made to commonly assigned U.S. Patent Pub. No. 2011/0085720, which is incorporated herein by reference, for a more detailed description of automatic registration techniques.

The automatic registration method includes moving locatable guide 86 containing position sensor 96 within a branched structure of a patient "P." Data pertaining to locations of the position sensor 96 with respect to the electromagnetic filed generated by the electromagnetic field transmitter 76 is recorded. A shape resulting from the data is compared to an interior geometry of passages of the three-dimensional model of the branched structure. And, a location correlation between the shape and the three-dimensional model based on the comparison is determined.

In addition to the foregoing, the software of the cytology sampling system 10 identifies non-tissue space (e.g., air filled cavities) in the three-dimensional model. Thereafter, the software records position data of the position sensor 96 of the locatable guide 86 as the locatable guide 86 is moved through one or more lumens of the branched structure. Further, the software aligns an image representing a location of the locatable guide 86 with an image of the three-dimensional model based on the recorded position data and an assumption that the locatable guide 86 remains located in non-tissue space in the branched structure.

Once in place in the patient "P," a screen 93 will be displayed by the software on the monitoring equipment 74

Figure 9:
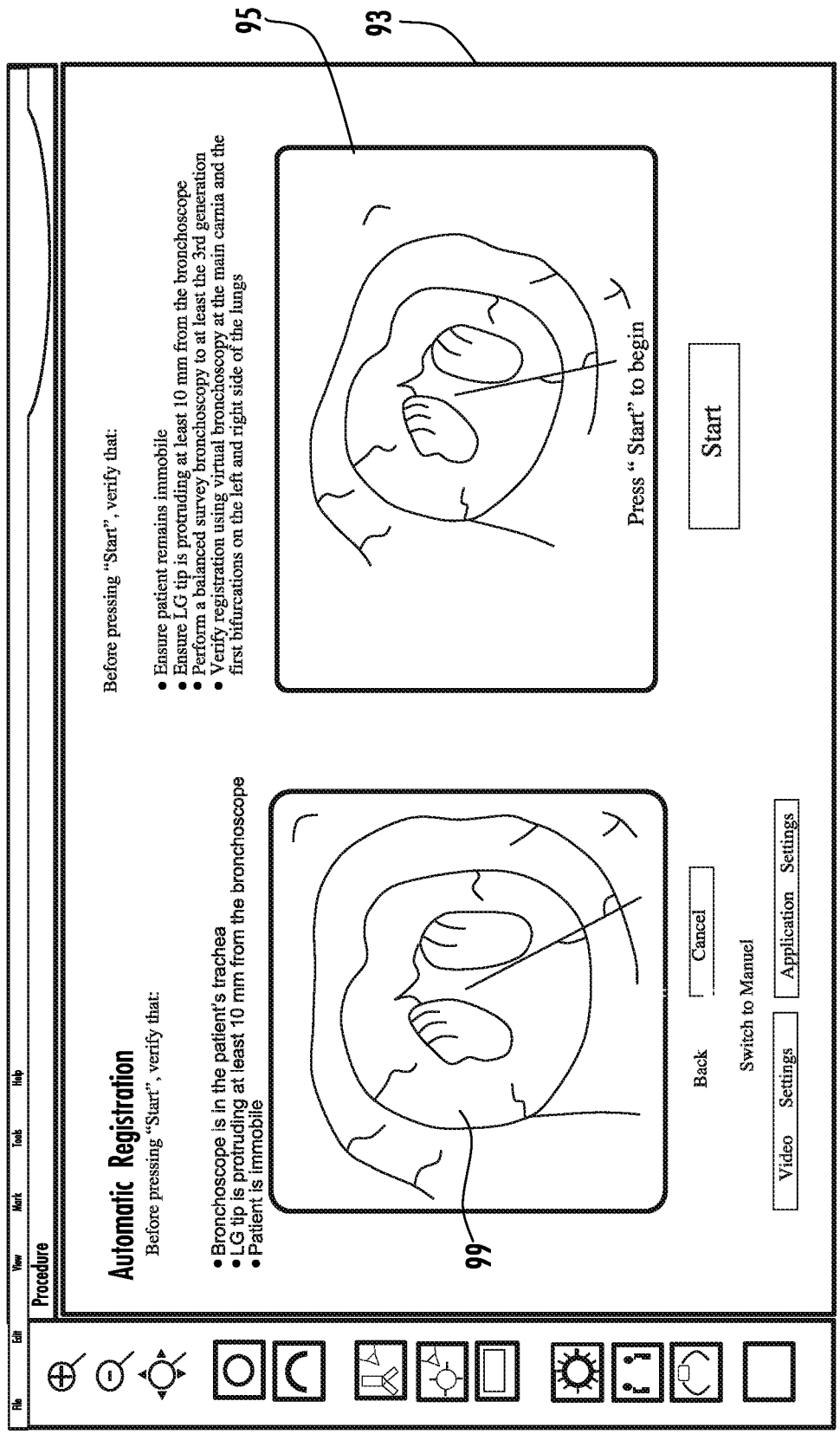
FIG. 9 is a screen shot of a CT based luminal navigation system in accordance with the present disclosure.

(FIG. 9). The right image is an actual bronchoscopic image 95 generated by the bronchoscope 72. Initially there is no image displayed in the left image 97, this will be a virtual bronchoscopy generated from the CT image data once registration is complete.

Starting with the locatable guide 86, and specifically the position sensor 96 approximately 3-4 cm above the main carina, as viewed through the bronchoscope 72, the bronchoscope 72 is advanced into both the right and left lungs to, for example, the fourth generation of the lung passages. By traversing these segments of the lungs, sufficient data is collected as described above such that registration can be accomplished.

Now that the targets have been identified, the pathway planned, the bronchoscope 72 including locatable guide 86 inserted into the patient "P," and the virtual bronchoscopy image registered with the image data of the bronchoscope 72, the cytology sampling system 10 is ready to navigate the position sensor 96 to the target 68 within the patient's lungs. The computer 82 (FIG. 5) provides a display for identifying the target 68 and depicting the virtual bronchoscopy image 99. Appearing in each of the images on the display is the pathway from the current location of the position sensor 96 to the target 68. This is the pathway that was established during the pathway planning phase discussed above. The pathway may be represented, for example, by a colored line. Also appearing in each image is a representation of the steerable distal tip 88 of the locatable guide 86 and position sensor 96. Once the steerable distal tip 88 traverses the established pathway, a clinician may utilize the cytology catheter assembly 12 to sample the target tissue 68 as detailed below.

Figure 11A:
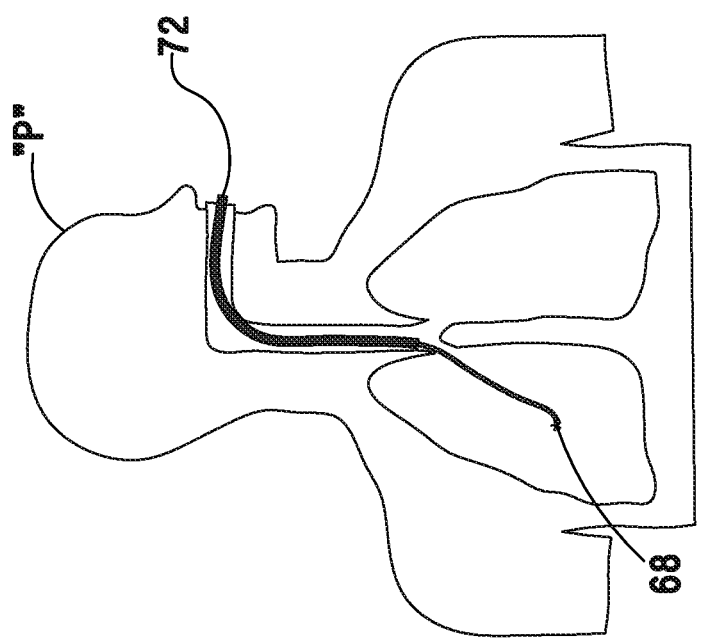
FIG. 11A is a schematic, plan view of the bronchoscope positioned within the trachea of the patient with the extended working channel extending distally therefrom.
Figure 11B:
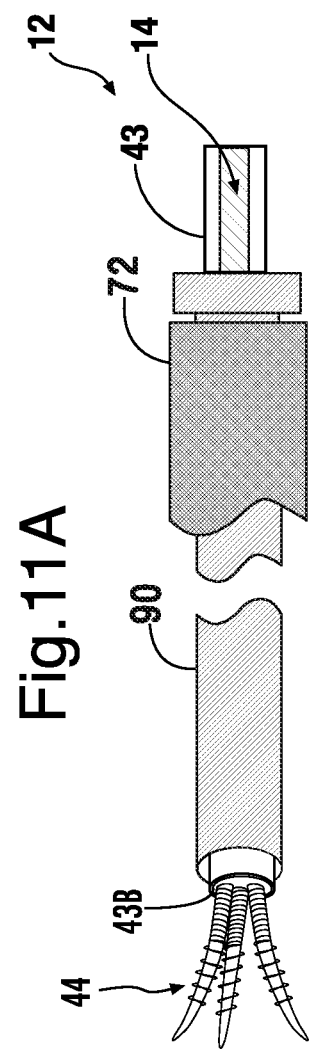
FIG. 11B is a partial, cutaway view of the extended working channel and the cytology catheter assembly of FIG. 1 positioned within the bronchoscope.

Operation of the cytology catheter assembly 12 with the positioning assembly 84 to sample target tissue is described with reference to FIGS. 10A-11B. Once the locatable guide 86 or an additional access tool has successfully been navigated to the target 68 location, the locatable guide 86 or access tool may be removed, leaving the extended working channel 90 in place as a guide channel for the cytology catheter assembly 12 (FIG. 1) to the target 68 location (FIGS. 11A-11B).

In some cases the target may be directly accessed from within the lumen (such as for the sampling of the endobronchial wall), however in other instances, the target is not within the BT and use of the locatable guide alone does not achieve access to the target. Additional access tools may be required to cross the lumen wall and access the target (such as for the sampling of disease within the parenchyma).

Final localization and confirmation of the locatable guide or access tool with extended working channel may be performed with imaging and/or navigational guidance (this may include the same or different combinations of imaging and navigation techniques listed above).

The catheter tube 43 is inserted through the working channel 90 such that the distal end 43b of the catheter tube 43 is adjacent the target 68. Alternatively, the catheter tube 43 or the cytology tool 14 may itself include a position sensor 88, such that the catheter tube 43 is already inserted through the working channel 90 during the positioning of extended working channel. The position sensor 88 may also be disposed on the distal end 43b of the catheter tube 43 or on the brush 44. The cytology tool 14 is inserted through the catheter tube 43 as detailed above to collect cell samples from the target 68. It is also contemplated that the cytology tool 14 may be inserted directly through working channel 90 without a catheter tube 43.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A cytology tool for placement within an airway of a patient's lung, comprising:
   a flexible shaft defining a longitudinal axis;
   a plurality of flexible brush shafts coupled to a distal end portion of the flexible shaft and biased away from the longitudinal axis, the plurality of flexible brush shafts configured to transition between a first configuration wherein the plurality of flexible brush shafts is urged into substantial alignment with the longitudinal axis and a second configuration wherein the plurality of flexible brush shafts is radially spaced from the longitudinal axis, a distal end of each flexible brush shaft of the plurality of flexible brush shafts forming a needle tip; and
   a plurality of nylon bristles disposed helically around each flexible brush shaft of the plurality of flexible brush shafts.

2. The cytology tool according to claim 1, wherein the needle tip of each flexible brush shaft of the plurality of flexible brush shafts is configured to penetrate a wall of an airway of a patient's lung for contacting target tissue with the plurality of nylon bristles.

3. The cytology tool according to claim 1, further comprising a flexible catheter tube, wherein the flexible shaft is configured to move longitudinally within the flexible catheter tube to transition the plurality of flexible brush shafts between the first and second configurations.

4. The cytology tool according to claim 3, wherein the outer diameter of the flexible catheter tube is in a range of about 1.5 mm to about 2.5 mm.

5. The cytology tool according to claim 3, wherein the length of the flexible catheter tube is in a range of about 60 cm to about 180 cm.

6. The cytology tool according to claim 1, wherein the plurality of flexible brush shafts includes three flexible brush shafts.

7. The cytology tool according to claim 1, wherein the length of each flexible brush shaft of the plurality of flexible brush shafts is in a range of about 10 mm to about 25 mm.

8. The cytology tool according to claim 1, wherein the length of each flexible brush shaft of the plurality of flexible brush shafts is greater than 0 mm and less than 10 mm.

9. The cytology tool according to claim 1, wherein the length of each flexible brush shaft of the plurality of flexible brush shafts is greater than 25 mm.

10. The cytology tool according to claim 1, wherein the outer diameter of each flexible brush shaft of the plurality of flexible brush shafts is in a range of about 0.5 mm to about 1.0 mm.

11. The cytology tool according to claim 1, wherein the plurality of nylon bristles extend radially away from the outer surface of each flexible brush shaft of the plurality of flexible brush shafts a distance in a range of about 0.25 mm to about 1.0 mm.

12. A cytology tool for placement within an airway of a patient's lung, comprising:
- a flexible catheter tube defining a longitudinal axis;
- a plurality of flexible brush shafts biased away from the longitudinal axis, the plurality of flexible brush shafts configured to move along the longitudinal axis relative to the flexible catheter tube between a first position wherein the plurality of flexible brush shafts is urged into substantial alignment with the longitudinal axis, and a second position wherein the plurality of flexible brush shafts is radially spaced from the longitudinal axis, a distal end of each flexible brush shaft of the plurality of flexible brush shafts forming a needle tip; and
- a plurality of nylon bristles disposed helically around each flexible brush shaft of the plurality of flexible brush shafts.

13. The cytology tool according to claim 12, wherein the needle tip of each flexible brush shaft of the plurality of flexible brush shafts is configured to penetrate a wall of an airway of a patient's lung for contacting target tissue with the plurality of nylon bristles.

14. The cytology tool according to claim 12, wherein the plurality of flexible brush shafts includes three flexible brush shafts.

15. The cytology tool according to claim 12, further comprising a flexible shaft coupled to the plurality of flexible brush shafts and configured to move longitudinally within the flexible catheter tube to move the plurality of flexible brush shafts between the first and second positions.

16. The cytology tool according to claim 12, wherein the length of each flexible brush shaft of the plurality of flexible brush shafts is in a range of about 10 mm to about 25 mm.

17. A cytology tool for placement within an airway of a patient's lung, comprising:
- a plurality of flexible brush shafts movable along a longitudinal axis between a first configuration wherein the plurality of flexible brush shafts is urged into substantial alignment with the longitudinal axis and a second configuration wherein the plurality of flexible brush shafts is radially spaced from the longitudinal axis, a distal end of each flexible brush shaft of the plurality of flexible brush shafts forming a needle tip; and
- a plurality of nylon bristles disposed around each flexible brush shaft of the plurality of flexible brush shafts, wherein the needle tip of each flexible brush shaft of the plurality of flexible brush shafts is configured to penetrate a wall of an airway of a patient's lung for contacting target tissue with the plurality of nylon bristles.

18. The cytology tool according to claim 17, wherein the length of each flexible brush shaft of the plurality of flexible brush shafts is in a range of about 10 mm to about 25 mm.

19. The cytology tool according to claim 17, wherein the plurality of nylon bristles are disposed helically around each flexible brush shaft of the plurality of flexible brush shafts.

20. The cytology tool according to claim 17, wherein the plurality of bristles extend radially away from an outer surface of each flexible brush shaft of the plurality of flexible brush shafts a distance in a range of about 0.25 mm to about 1.0 mm.

\* \* \* \* \*